(12) United States Patent
Kim et al.

(10) Patent No.: US 8,158,168 B2
(45) Date of Patent: Apr. 17, 2012

(54) **ANTI-GASTRITIS AND ANTI-ULCER AGENT CONTAINING *MOMORDICAE SEMEN* EXTRACT AND MOMORDICA SAPONIN I ISOLATED FROM THE SAME**

(75) Inventors: Bong Cheol Kim, Gyeonggi-do (KR); Joo Hyon Kim, Gyeonggi-do (KR); Se Jun Yun, Seoul (KR); Eun Jung Noh, Seoul (KR); Gi Uk Jang, Seoul (KR); Chang-Kyun Han, Seoul (KR); Yong-Baik Cho, Gyeonggi-do (KR); Wie-Jong Kwak, Seoul (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 61 days.

(21) Appl. No.: 12/857,035

(22) Filed: Aug. 16, 2010

(65) Prior Publication Data
US 2010/0310687 A1  Dec. 9, 2010

Related U.S. Application Data

(62) Division of application No. 12/096,881, filed as application No. PCT/KR2006/005603 on Dec. 20, 2006, now abandoned.

(30) Foreign Application Priority Data

Dec. 20, 2005  (KR) .................. 10-2005-0126302
Dec. 14, 2006  (KR) .................. 10-2006-0128138

(51) Int. Cl.
    *A01N 65/00*  (2009.01)
(52) U.S. Cl. ........................................ 424/725
(58) Field of Classification Search .................. None
    See application file for complete search history.

(56) References Cited

FOREIGN PATENT DOCUMENTS

| CN | 1260985 | * | 7/2000 |
| JP | 410059858 | | 3/1998 |
| JP | 11-302180 A | | 11/1999 |
| KR | 1995-0007046 B | | 6/1995 |
| KR | 1996-0012276 B | | 9/1996 |
| KR | 0181751 | | 5/1999 |
| KR | 10-2003-0021714 A | | 3/2003 |

OTHER PUBLICATIONS

Herbs for external use and others, 3 pages, 2011.*
Suzuki, Masayuki et al.: "Role of ammonia-monochloramine system in *Helicobacter pylori*-induced gastric mucosal injury", *Helicobacter pylori*, 51, 12,1993, pp. 3154-3158 in Korean with English translation of summary.
Mizuno, Tadaoki: "Easy Ulcerative Tendency of the Stomach in Hypotensive Patients", *Yokohama Med. Bull.*, vol. 38, Nos. 3-4, 198, pp. 87-97.
Schunack, W.: "Pharmacology of $H_2$-receptor Antagonists: an Overview", *The Journal of International Medical Research*, 1989: 17 (suppl. 1) pp. 9A-16A.
Mills, Jane G. et al. : "The Pharmacology of Histamine $H_2$-Receptor Antagonists", *Meth. Find. Exp. Clin. Pharmacol.*, 1989, 11 (suppl. 1), pp. 87-95.
Feldman M.D., Mark et al.: "$Histamine_2$-Receptor Antagonists", *The New England Journal of Medicine*, vol. 323, No. 24, Dec. 13, 1990, pp. 1672-1680.
Berardi, Rosemary R. et al.: "Maintenace Therapy for Prevention of Recurrent Peptic Ulcers", *Drug Intelligence and Clinical Pharmacy*, Jun. 1987, vol. 21, pp. 493-501.
Fullarton, G.M. et al.: "Rebound nocturnal hypersecretion after four weeks treatment with an $H_2$ receptor antagonist", *Gut*, 1989, 30, pp. 449-454.
Bell, Nicholas J.V. et al.: "Progress with Proton Pump Inhibition", *The Yale Journal of Biology and Medicine*, 65 (1992), pp. 649-657.

* cited by examiner

*Primary Examiner* — Michael Meller
(74) *Attorney, Agent, or Firm* — Frommer Lawrence & Haug LLP; Ronald R Santucci

(57) ABSTRACT

The present invention relates to a Momordicae semen extract effective in the prevention and treatment of gastritis or gastric ulcer and *momordica* saponin I isolated therefrom. The Momordicae semen extract and the *momordica* saponin I isolated therefrom is effective in the prevention and treatment of gastritis or gastric ulcer since they prevent the damage of the gastric mucosa caused by alcohols and inhibit the secretion of gastric acid.teh

5 Claims, No Drawings

ANTI-GASTRITIS AND ANTI-ULCER AGENT CONTAINING *MOMORDICAE SEMEN* EXTRACT AND MOMORDICA SAPONIN I ISOLATED FROM THE SAME

This application is a division of U.S. patent application Ser. No. 12/096,881 filed Aug. 21, 2008 entitled "Anti-Gastritis and Anti-Ulcer Agent Containing Momordicae Semen Extract and *Momordica* Saponin I Isolated from the Same" which is a 371 filing of PCT/KR2006/005603 filed Dec. 20, 2006 and which claims priority to Korean Application Number KR 10-2005-0126302 filed Dec. 20, 2005 and Korean Application Number KR 10-2006-0128138 filed Dec. 14, 2006, the disclosures of which are hereby incorporated by reference.

TECHNICAL FIELD

The present invention relates to a Momordicae semen extract effective in the prevention and treatment of gastritis or gastric ulcer and *momordica* saponin I isolated therefrom.

BACKGROUND ART

The gastric mucosal layer which protects the stomach can be easily damaged by various factors. Typical factors of such include gastric acid, alcohols, non-steroidal anti-inflammatory drugs (NSAID) such as aspirin, bacteria such as *Helicobacter pylori* [Suzuki. M. and S. Miura, *Nippon Rinsho*, 15(12), 3154-3158, 1993], disturbance of microcirculation of gastric mucosa and hypotension caused by stress [Tadaoki Mizuno, *Yokohama Med. Bull.*, 38(3,4), 87-97, 1987], etc. When the mucosal layer is damaged by the above factors, there occurs inflammation which is accompanied by flare, hemorrhage and edema. In severe cases, this may lead to damage in the submucosa and the muscle layer, called gastric ulcer. Further, the duodenum which is in direct contact with the stomach may get inflammation or ulcer because of the exposure to similar factors.

For the treatment of the inflammation and ulcer of the stomach and the duodenum caused by these factors, it is essential to develop a drug effective in inhibiting the secretion of gastric acid, inhibiting the proliferation of *Helicobacter pylori*, stimulating the secretion of mucus, promoting the regeneration of epithelial cells, fighting against inflammation, etc. At present, the most typical treatments for gastritis and gastric ulcer are H2 antagonists and proton pump inhibitors effective in inhibiting the secretion of gastric acid. These drugs are shown to have superior clinical effect [*J. Int. Med. Res.* 17(suppl.) 9A, 1989; *Meth. Find. Exp. Clin. Pharmacol.* 11(suppl. 1) 87, 1989; *N. Eng. J. Med.* 323: 1672, 1990]. However, these gastric acid secretion inhibitors have a drawback that the condition recurs when the administration of the drugs is stopped [*Drug Intell. Clin. Pharm.* 21: 493, 1987, *Gut* 30: 449, 1989 *Yale J. Biol. Med.* 65: 649, 1992].

The mucosal protectant, which promotes the regeneration of the mucosal tissue to ensure protection against the re-attack of gastritis inducing factors to reduce the recurrence of gastritis, is an important component of the gastritis treatment. Currently, such drugs as rebamipide, sofalcone, etc., are available as a gastric mucosal protectant. However, they should be taken in large amount for a long period of time due to the rather slow actions of these drugs, and thus there is a need for the development of improved drugs.

One of the most commonly used methods of assessing the efficiency of gastritis treatment using an animal model is to introduce damage on the gastric mucosa by using non-steroidal anti-inflammatory drugs (NSAID) or ethanol, and observe the rate of recovery. Through these animal model tests, various herbal extracts have been reported as candidates for the treatment of gastritis. In particular, the extract of *Artemisia* Spps having superior effect in treating gastritis has been applied for a patent [Korean Patent Application No. 10-1995-0021957] and developed as a commercial drug named Stillen® by Dong-A Pharmaceutical.

The Momordicae semen used in the present invention is a ripe seed of *Momordica*, a perennial vine which grows widely in southern China and Vietnam. Fruits harvested between September and November are cut in half and the seeds are collected when they are half dry. Or, the fruits are put into jars and the seeds are taken when the rinds become rotten. Momordicae semen is known to have good anti-inflammatory activity and be effective against rheumatic pain, muscular spasm, etc. At present, the Momordicae semen extract is known to contain sterol, oleanolic acid, momordic acid, etc.

The present inventors have made extensive efforts to develop a treatment for gastritis. In doing so, they discovered that the Momordicae semen extract and *momordica* saponin I isolated therefrom reduce the damage of the gastric mucosa induced by diclofenac and alcohols in rats. They also discovered that the administration of Momordicae semen extract and *momordica* saponin I reduces the acidity in the stomach.

Accordingly, an object of the present invention is to provide a drug for the prevention and treatment of gastritis or gastric ulcer comprising Momordicae semen extract or *momordica* saponin I as an active ingredient which is superior in protecting the gastric mucosa and inhibiting gastric acid.

DISCLOSURE OF THE INVENTION

The present invention relates to a drug for the prevention and treatment of gastritis or gastric ulcer comprising Momordicae semen extract as an active ingredient.

The present invention also relates to a drug for the prevention and treatment of gastritis or gastric ulcer comprising *momordica* saponin I, which is represented by the following formula (1), as an active ingredient.

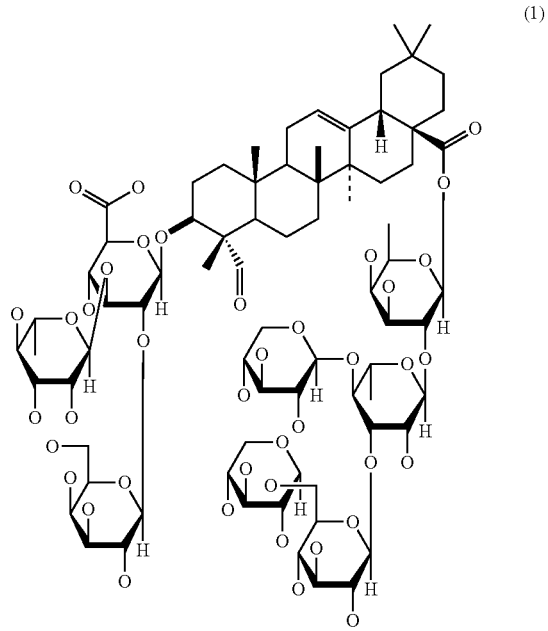

Hereunder is given a more detailed description of the present invention.

The present invention relates to a drug comprising Momordicae semen extract and *momordica* saponin I isolated therefrom, which are effective in the prevention and treatment of gastritis or gastric ulcer with good inhibition activity against the damage of gastric mucosa caused by alcohols and non-steroidal anti-inflammatory drugs (NSAID) such as diclofenac and good inhibition activity against the secretion of gastric acid.

The Momordicae semen extract of the present invention is obtained by extracting the herb Momordicae semen 3-10 weight equivalents of water or alcohol solution, according to the common method used to extract herbs. Preferably, said alcohol is $C_1$-$C_6$ alcohol, more preferably, methanol, ethanol, butanol, etc.

The Momordicae semen extract is lyophilized to obtain the extract in powder form. With good activity for the prevention and treatment of the damage of gastric mucosa induced by diclofenac and alcohols, this extract is expected to be very useful as a drug for the prevention and treatment of gastritis or gastric ulcer.

In addition, the *momordica* saponin I of the present invention can be efficiently isolated from Momordicae semen by the common method using polar solvent. For the polar solvent, distilled water or alcohol solution may be used. Preferably, the alcohol is a $C_1$-$C_6$ alcohol, more preferably, methanol, ethanol, butanol, etc.

Particularly, column chromatography may be performed to obtain *momordica* saponin I with better purity. More specifically, a chromatography column is prepared using octadecylsilylated silica resin, etc. and such adequate solvent as 70% (v/v) aqueous methanol solution, etc. is used to selectively separate the fraction with a high saponin concentration.

With superior effect of preventing and treating the damage of gastric mucosa induced by alcohol or diclofenac and good effect of preventing the secretion of gastric acid, *momordica* saponin I is a good candidate for the drug for the prevention and treatment of gastritis or gastric ulcer.

The Momordicae semen extract or *momordica* saponin I of the present invention is prepared into tablet or capsule by the common method. In case of tablets, one having activity for the prevention and treatment of gastritis or gastric ulcer can be prepared using a matrix comprising lactose, microcrystalline cellulose, magnesium stearate, etc., and an active ingredient, or the Momordicae semen extract or *momordica* saponin I of the present invention, at a proportion of 2-10 to 1.

The active ingredient may be used either in itself or after mixing with a pharmaceutically acceptable carrier, a forming agent, a diluent to obtain the formulation in the form of powder, granules, capsules, etc. The dosage of Momordicae semen extract or *momordica* saponin I of the present invention may vary depending on absorption rate, body weight, age, sex, physical conditions, diet, administration time, type of administration, severity of disease, and the like. As a general rule, about 0.1-10 mg per 1 kg of body weight is preferable for the Momordicae semen extract and about 0.05-1 mg per 1 kg of body weight is preferable for the *momordica* saponin I. The drug in the unit dosage form may be administered through a customized medication plan or several times with predetermined intervals, depending on the decision of an expert who monitors the administration or on the demand of the patients.

BEST MODE FOR CARRYING OUT THE INVENTION

Practical and presently preferred embodiments of the present invention are illustrative as shown in the following examples. However, it will be appreciated that those skilled in the art may, in consideration of this disclosure, make modifications and improvements within the spirit and scope of the present invention.

PREPARATIVE EXAMPLE 1

Preparation of Momordicae Semen Extract

To 1 kg (dry weight) of Momordicae semen purchased from at the herb market was added 5 L of 50% aqueous ethanol solution. Extraction was performed for 4 hours while maintaining the temperature at 80° C. This procedure was repeated twice to obtain the herb extract. The extract was filtered and concentrated under reduced pressure at 60° C. using a rotary evaporator. Then, after completely removing the solvent in a vacuum oven, 21 g of ethanol extract in powder form was obtained.

PREPARATIVE EXAMPLE 2

Preparation of Extract Containing *Momordica* Saponin I 1 kg (dry weight) of Momordicae semen purchased from at the herb market was crushed and 5 L of 10% aqueous ethanol solution was added. Extraction was performed for 3 hours in a water bath kept at 80° C. This procedure was repeated twice. The extract was filtered and concentrated under reduced pressure at 60° C. using a rotary evaporator. Then, after completely removing the solvent in a vacuum oven, 35-45 g of extract containing *momordica* saponin I was obtained in powder form.

PREPARATIVE EXAMPLE 3

Preparation of *Momordica* Saponin I Fraction

*Momordica* saponin I was effectively isolated from the extract prepared in Preparative Example 2 through precipitation using organic solvent (acetone). 10 g of the extract prepared in Preparative Example 2 was dissolved in 100 mL of purified water and 100 mL of acetone was added to obtain 50% (v/v) aqueous acetone solution. Precipitate was filtered off and 400 mL of acetone was further added to the filtrate to obtain 80% (v/v) aqueous acetone solution. The newly formed precipitate was separated using a filter paper and dried.

PREPARATIVE EXAMPLE 4

Preparation of *Momordica* Saponin I Fraction

Column chromatography was performed on the extract prepared in Preparative Example 2 or the fraction obtained in Preparative Example 3 using octadecylsilylated silica resin (YMC*GEL ODS-A 12 nm, S-150 m). The amount of the resin was 250 g, or 25 times the weight of the extract or the fraction. Each of 10% (v/v) and 40% (v/v) aqueous methanol solution, which is 2-3 times the volume of the resin, was flown and then 70% (v/v) aqueous methanol solution, which is 2-3 times the volume of the resin, was flown. The resultant elution fraction was concentrated under reduced pressure and the solvent was completely removed in a vacuum oven.

PREPARATIVE EXAMPLE 5

Isolation of *momordica* Saponin I

*Momordica* saponin I was isolated from the 70% (v/v) aqueous methanol solution fraction of Preparative Example 4. High performance liquid chromatography was performed using a mixed solvent of acetonitrile and water (29:71, 0.1% trifluoroacetic acid). Elution was performed at a rate of 9.5 mL/min and the saponin peak was taken at about 45 minutes. This fraction was concentrated under reduced pressure and the solvent was completely removed in a vacuum oven. YMC J'Sphere ODS-H80 column was used and the measurement was made at 210 nm.

Mass spectroscopy and NMR spectroscopy data were compared with those presented in the literature [Iwamoto, Okabe, Yamauchi, Tanaka, Rokutani, Hara, Mihashi, Higuchi. Studies on the constituents of *Momordica* cochinchinensis Spreng. I. Isolation and characterization of the seed saponins, momordica saponin I and II. *Chemical & Pharmaceutical Bulletin* 1985, 33(2):464-478]. The data coincided with those of *momordica* saponin I (3-O-β-D-galactopyranosyl(1->2)-[α-L-rhamnopyranosyl(1->3)]-β-D-glucuronopyranosido-28-O-β-D-xylopyranosyl(1->3)-β-D-glucopyranosyl(1->3)-[β-D-xylopyranosyl(1->4)]-α-L-rhamnopyranosyl(1->2)-β-D-fucopyranosylgypsogenin), which is known to be present in Momordicae semen.

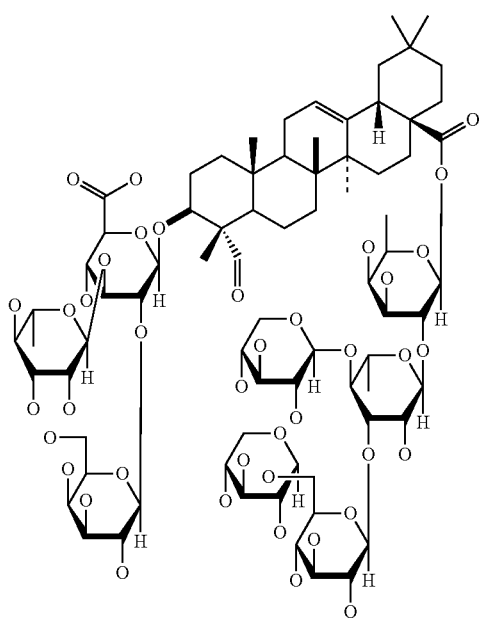

(1)

Molecular weight: 1673.77

Melting point: 241-244° C.

Optical rotation: [α]19 D=−14.8° (C 0.7, MeOH:H$_2$O=1:2)

The contents of *momordica* saponin I in the extract or the fraction of Preparative Examples 2 to 4 are given in Table 1 below.

TABLE 1

| Category | Preparative Example 2 | Preparative Example 3 | Preparative Example 4 |
| --- | --- | --- | --- |
| Contents of *momordica* saponin I (%) | 7-14 | 13-25 | 40-50 |

EXAMPLE 1

Protective Effect of Momordicae Semen Extract Against the Stomach Damage Induced by Alcohol A rat model test was performed using 100% ethanol as stomach damage inducing factor to evaluate the protective effect of the *Momordicae* semen extract for gastric mucosa. The Momordicae semen extract of Preparative Example 1 was dissolved in 0.5% aqueous carboxymethyl cellulose solution to 10 mg/mL and was used as a test drug. Stillen (artemisia extract, Dong-A Pharmaceutical) and Mucosta (rebamipide, Korea Otsuka Pharmaceuticals) dissolved in 0.5% aqueous carboxymethyl cellulose solution to 10 mg/mL were used as control drugs.

Seven-week-old specific pathogen free (SPF) male Sprague-Dawley rats were purchased from Charles River. After 1 week of adaptation, healthy rats with a weight of 220-225 g were selected for the test. Five rats per each group were fasted for 18 hours with drinking water freely available. The Momordicae semen extract and the control drugs Stillen and Mucosta were administered at a dosage of 100 mg/kg. After 1 hour, 1.5 mL of 100% ethanol was orally administered. 6 hours later, the rats were anesthetized with ether and the stomach was taken out in order to evaluate the drug's effect of preventing the stomach damage. The stomach was cut open along the greater curvature and was observed with eyes. The damage of the stomach was categorized into flare, congestion, hemorrhage, inflammation and edema. The severity of the damage was evaluated with points ranging from 0 to 3.

TABLE 2

| | Damage of gastric mucosa (gastric mucosa damage index) | | | | | |
| --- | --- | --- | --- | --- | --- | --- |
| Category | Flare | Hyperemia | Bleeding | Erosion | Edema | Total |
| Water | 1.8 ± 0.2 | 1.6 ± 0.2 | 2.4 ± 0.4 | 1.8 ± 0.4 | 1.8 ± 0.4 | 9.4 ± 1.3 |
| Stillen | 1.8 ± 0.2 | 1.4 ± 0.2 | 1.0 ± 0.5 | 1.2 ± 0.2 | 1.2 ± 0.4 | 7.7 ± 1.2 |
| Mucosta | 1.3 ± 0.2 | 1.3 ± 0.4 | 1.5 ± 0.2 | 1.8 ± 0.2 | 1.3 ± 0.2 | 8.1 ± 0.8 |
| *Momordicae semen* extract | 1.0 ± 0.3 | 1.0 ± 0.3 | 0.8 ± 0.2 | 1.5 ± 0.2 | 1.0 ± 0.3 | 6.4 ± 1.3 |

As seen in Table 2, the Momordicae semen extract had superior effect of preventing the damage of gastric mucosa induced by alcohol.

EXAMPLE 2

Protective Effect of *Momordica* Saponin I Against the Stomach Damage Induced by Alcohol A rat model test was performed using 100% ethanol as stomach damage inducing factor to evaluate the protective effect of *momordica* saponin I for gastric mucosa. The *momordica* saponin I isolated in Preparative Example 5 was dissolved in 0.5% aqueous carboxymethyl cellulose solution to 2 mg/mL and was used as a test drug. Mucosta (rebamipide, Korea Otsuka Pharmaceuticals) dissolved in 0.5% aqueous carboxymethyl cellulose solution to 10 mg/mL was used as control drug.

Seven-week-old specific pathogen free (SPF) male Sprague-Dawley rats were purchased from Charles River. After 1 week of adaptation, healthy rats with a weight of 220-225 g were selected for the test. Five rats per each group were fasted for 18 hours with drinking water freely available. *Momordica* saponin I were administered at a dosage of 20 mg/kg and the control drug Mucosta were administered at a dosage of 100 mg/kg. After 30 minutes, 1.5 mL of 100% ethanol was orally administered. 3 hours later, the rats were anesthetized with ether and the stomach was taken out in order to evaluate the drug's effect of preventing the stomach damage. The stomach was cut open along the greater curvature and was observed with eyes. The damage of the stomach was classified into flare, congestion, hemorrhage, inflammation and edema. The severity of the damage was evaluated with points ranging from 0 to 3 (the higher the point, the severer the damage.).

As seen in Table 3, *momordica* saponin I had superior effect of preventing the damage of gastric mucosa induced by alcohol.

EXAMPLE 3

Healing Effect of *Momordicae* Semen Extract on the Stomach Damage Induced by Diclofenac A rat model test was performed using diclofenac, a representative non-steroidal anti-inflammatory drug (NSAID), as stomach damage inducing factor to evaluate the effect of the Momordicae semen extract of Example 1 for treating gastritis. The Momordicae semen extract was dissolved in 0.5% aqueous carboxymethyl cellulose solution to 10 mg/mL and was used as a test drug. Stillen (artemisia extract, Dong-A Pharmaceutical) and Mucosta (rebamipide, Korea Otsuka Pharmaceuticals) dissolved in 0.5% aqueous carboxymethyl cellulose solution to 10 mg/mL were used as control drugs.

Seven-week-old specific pathogen free (SPF) male Sprague-Dawley rats were purchased from Charles River. After 1 week of adaptation, healthy rats with a weight of 220-225 g were selected for the test. Five rats per each group were fasted for 18 hours with drinking water freely available and diclofenac was orally administered at a dosage of 40 mg/kg.

TABLE 3

| Damage of gastric mucosa (gastric mucosa damage index ± standard deviation) | | | | | | |
| --- | --- | --- | --- | --- | --- | --- |
| Category | Flare | Hyperemia | Bleeding | Erosion | Edema | Total |
| Water | 1.9 ± 0.3 | 1.5 ± 0.3 | 2.5 ± 0.5 | 0.7 ± 0.2 | 1.3 ± 0.2 | 7.9 ± 1.5 |
| Mucosta | 1.2 ± 0.2 | 1.4 ± 0.2 | 1.4 ± 0.2 | 0.9 ± 0.3 | 1.2 ± 0.3 | 6.1 ± 1.2 |
| *Momordica* saponin I | 1.1 ± 0.2 | 0.9 ± 0.3 | 0.9 ± 0.2 | 0.5 ± 0.1 | 1 ± 0.3 | 4.4 ± 1.1 |

After 6 hours of stomach damage inducement, the Momordicae semen extract and the control drugs Stillen and Mucosta were administered at a dosage of 100 mg/kg. 18 hours later, the rats were anesthetized with ether and the stomach was taken out in order to evaluate the drug's effect of treating gastritis. The stomach was cut open along the greater curvature and was observed with eyes. The damage of the stomach was classified into flare, congestion, hemorrhage, inflammation and edema. The severity of the damage was evaluated with points ranging from 0 to 3.

TABLE 4

| Damage of gastric mucosa (gastric mucosa damage index) | | | | | | |
| --- | --- | --- | --- | --- | --- | --- |
| Category | Flare | Hyperemia | Bleeding | Erosion | Edema | Total |
| Water | 2.6 ± 0.2 | 2.4 ± 0.4 | 2.6 ± 0.2 | 2.6 ± 0.2 | 2.2 ± 0.2 | 12.4 ± 0.7 |
| Stillen | 1.0 ± 0.4 | 1.8 ± 0.2 | 1.4 ± 0.2 | 3.0 ± 0.0 | 2.6 ± 0.2 | 9.8 ± 0.5 |
| Mucosta | 0.8 ± 0.4 | 0.8 ± 0.4 | 1.2 ± 0.2 | 2.4 ± 0.2 | 2.2 ± 0.2 | 7.4 ± 0.7 |
| *Momordicae semen* extract | 0.0 ± 0.0 | 0.6 ± 0.2 | 0.6 ± 0.2 | 1.2 ± 0.2 | 1.2 ± 0.4 | 3.6 ± 0.2 |

As seen in Table 4, the Momordicae semen extract of Preparative Example 1 had superior effect in treating the damaged gastric mucosa.

EXAMPLE 4

Protective Effect of Momordicae Semen Extract Against the Stomach Damage Induced by Diclofenac Differently from Example 3, diclofenac and the test drug were administered simultaneously and the damage of gastric mucosa was observed 6 hours later. In order to prevent the direct interaction between diclofenac and the test drug, the test drug was administered abdominally. Similar to that in Example 3, diclofenac and the test drug were dissolved in 0.5% aqueous carboxymethyl cellulose solution to 10 mg/mL.

Seven-week-old specific pathogen free (SPF) male Sprague-Dawley rats were purchased from Charles River. After 1 week of adaptation, healthy rats with a weight of 220-225 g were selected for the test. Five rats per each group were fasted for 18 hours with drinking water freely available and diclofenac was orally administered at a dosage of 40 mg/kg and, at the same time, the test drug, or the Momordicae semen extract, and the control drugs Stillen and Mucosta were abdominally administered at a dosage of 100 mg/kg. 6 hours later, the rats were anesthetized with ether and the stomach was taken out in order to evaluate the drug's effect of treating gastritis. The stomach was cut open along the greater curvature and was observed with eyes. The damage of the stomach was classified into flare, congestion, hemorrhage, inflammation and edema. The severity of the damage was evaluated with points ranging from 0 to 3.

TABLE 5

Damage of gastric mucosa (gastric mucosa damage index)

| Category | Flare | Hyperemia | Bleeding | Erosion | Edema | Total |
| --- | --- | --- | --- | --- | --- | --- |
| Water | 2.2 ± 0.4 | 1.4 ± 0.2 | 2.4 ± 0.4 | 2.4 ± 0.4 | 2.0 ± 0.3 | 10.4 ± 1.4 |
| Stillen | 1.8 ± 0.5 | 0.8 ± 0.2 | 1.4 ± 0.2 | 1.8 ± 0.2 | 1.6 ± 0.2 | 7.4 ± 1.2 |
| Mucosta | 2.6 ± 0.2 | 2.2 ± 0.4 | 1.4 ± 0.5 | 2.4 ± 0.4 | 1.2 ± 0.2 | 9.8 ± 1.2 |
| Momordicae semen extract | 1.6 ± 0.4 | 0.8 ± 0.4 | 0.8 ± 0.4 | 1.2 ± 0.2 | 1.4 ± 0.2 | 5.8 ± 1.4 |

As seen in Table 5, the Momordicae semen extract had the effect of treating the damaged gastric mucosa in addition to the capability of reducing the damage of gastric mucosa induced by NSAIDs, when administered along with NSAIDs such as diclofenac.

EXAMPLE 5

Protective Effect of Momordica Saponin I Against the Stomach Damage Induced by Diclofenac Diclofenac and the test drug were administered simultaneously and the damage of gastric mucosa was observed 4 hours later. Diclofenac was dissolved in 0.5% aqueous carboxymethyl cellulose solution to 40 mg/mL and the test drug was prepared as in Example 2.

Seven-week-old specific pathogen free (SPF) male Sprague-Dawley rats were purchased from Charles River. After 1 week of adaptation, healthy rats with a weight of 220-225 g were selected for the test. Five rats per each group were fasted for 18 hours with drinking water freely available and diclofenac was orally administered at a dosage of 40 mg/kg and, at the same time, the test drug, or momordica saponin I, was orally administered at a dosage of 20 mg/kg and the control drug Mucosta was orally administered at a dosage of 100 mg/kg. 4 hours later, the rats were anesthetized with ether and the stomach was taken out in order to evaluate the drug's effect of treating gastritis. The stomach was cut open along the greater curvature and was observed with eyes. The damage of the stomach was classified into flare, congestion, hemorrhage, inflammation and edema. The severity of the damage was evaluated with points ranging from 0 to 3 (The higher the point, the severer the damage).

TABLE 6

Damage of gastric mucosa (gastric mucosa damage index ± standard deviation)

| Category | Flare | Hyperemia | Bleeding | Erosion | Edema | Total |
| --- | --- | --- | --- | --- | --- | --- |
| Water | 2 ± 0.3 | 1.5 ± 0.3 | 2.6 ± 0.3 | 2.8 ± 0.5 | 1.4 ± 0.2 | 10.3 ± 1.6 |
| Mucosta | 2.3 ± 0.3 | 1.3 ± 0.4 | 1.5 ± 0.3 | 2.2 ± 0.4 | 1.2 ± 0.1 | 8.5 ± 1.5 |
| Momordica saponin I | 1.3 ± 0.2 | 0.9 ± 0.3 | 0.7 ± 0.2 | 1.3 ± 0.3 | 1 ± 0.2 | 5.2 ± 1.2 |

As seen in Table 6, momordica saponin I had the ability of reducing the damage of gastric mucosa caused by NSAIDs such as diclofenac.

EXAMPLE 6

Gastric Acid Secretion Inhibition Test for *Momordica* Saponin I in Rats

*Momordica* saponin I was orally administered to Sprague-Dawley rats and the acidity in the stomach was measured in order to evaluate the effect of *momordica* saponin I on the secretion of gastric acid. The *momordica* saponin I isolated in Preparative Example 4 was dissolved in 0.5% aqueous carboxymethyl cellulose solution to concentrations of 0.5, 1.5 and 4.5 mg/mL. 7-week-old specific pathogen free (SPF) male Sprague-Dawley rats were purchased from Charles River. After 1 week of adaptation, healthy rats with a weight of 220-225 g were selected for the test. Two rats per each group were fasted for 18 hours with drinking water freely available and *momordica* saponin I were administered at dosages of 5, 15 and 45 mg/kg. 1 hour later, the rats were anesthetized with ether. 0.5 mL of the gastric juice taken from the stomach was diluted 10 times with distilled water to obtain a 5 mL sample. The pH of the diluted gastric juice was measured with a pH meter.

TABLE 7

Acidity in the stomach of rats (pH ± standard deviation)

| | *Momordica* saponin I | | |
|---|---|---|---|
| Vehicle | 5 mg/kg | 15 mg/kg | 45 mg/kg |
| 2.3 ± 0.6 | 3.3 ± 0.1 | 4.3 ± 0.8 | 5.2 ± 0.6 |

As seen in Table 7, *momordica* saponin I effectively reduced the acidity of the gastric juice and thus can be useful in treating gastritis or gastric ulcer.

EXAMPLE 7

Acute Toxicity Test for Oral Administration of Momordicae Semen Extract in Rats Acute toxicity test was performed as follows using 6-week-old specific pathogen free (SPF) Sprague-Dawley rats To two rats per each group, the Momordicae semen extract prepared in Preparative Example 1 was orally administered once at a dosage of 1 g/kg. Survival, clinical manifestations and body weight change were observed and hematological and serum biochemical analysis was performed. Autopsy was performed to observe abnormalities in abdominal and thoracic organs. There was no noticeable clinical manifestation or death. In addition, no toxicity was found in body weight change, hematological and serum biochemical analysis and autopsy. The Momordicae semen extract of the present invention showed no toxicity in all rats up to the dosage of 2,000 mg/kg and was proved to be a safe substance with a minimum oral administration lethal dose ($LD_{50}$) of 2,000 mg/kg or larger.

EXAMPLE 8

Acute Toxicity Test for Oral Administration of *Momordica* Saponin I in Rats Acute toxicity test was performed as follows using 6-week-old specific pathogen free (SPF) Sprague-Dawley rats To two rats per each group, the *momordica* saponin I isolated in Preparative Example 5 was orally administered once at a dosage of 400 mg/kg. Survival, clinical manifestations and body weight change were observed and hematological and serum biochemical analysis was performed. Autopsy was performed to observe abnormalities in abdominal and thoracic organs. There was no noticeable clinical manifestation or death. In addition, no toxicity was found in body weight change, hematological and serum biochemical analysis and autopsy. The *momordica* saponin I of the present invention showed no toxicity in all rats up to the dosage of 400 mg/kg and was proved to be a safe substance with a minimum oral administration lethal dose ($LD_{50}$) of 400 mg/kg or larger.

PREPARATION EXAMPLE 1

Preparation of Tablet Containing *Momordicae* Semen Extract

The Momordicae semen extract of the present invention was prepared into tablet for oral administration by wet granulation and dry granulation.

[Composition]

Momordicae semen extract (200 mg), light anhydrous silica acid (10 mg), magnesium stearate (2 mg), microcrystalline cellulose (50 mg), sodium starch glycolate (25 mg), cornstarch (113 mg), anhydrous ethanol (adequate).

PREPARATION EXAMPLE 2

Preparation of Tablet Containing *Momordica* Saponin I

The *momordica* saponin I of the present invention was prepared into tablet for oral administration by wet granulation and dry granulation.

[Composition]

*Momordica* saponin 1 (20 mg), light anhydrous silica acid (10 mg), magnesium stearate (2 mg), microcrystalline cellulose (50 mg), sodium starch glycolate (25 mg), cornstarch (113 mg), anhydrous ethanol (adequate).

PREPARATION EXAMPLE 3

Preparation of Ointment Containing Momordicae Semen Extract

The Momordicae semen extract of the present invention was prepared into ointment.

[Composition]

Momordicae semen extract (5 g), cetyl palmitate (20 g), cetanol (40 g), stearyl alcohol (40 g), isopropyl myristate (80 g), sorbitan monostearate (20 g), polysorbate (60 g), propyl p-hyroxybenzoate (1 g), methyl p-hyroxybenzoate (1 g), phosphoric acid and purified water (adequate).

PREPARATION EXAMPLE 4

Preparation of Injection Containing Momordicae Semen Extract

The Momordicae semen extract of the present invention was prepared into injection.

[Composition]

Momordicae semen extract (100 mg), mannitol (180 mg), dibasic sodium diphosphate (25 mg), water for injection (2974 mg)

PREPARATION EXAMPLE 5

Preparation of Transdermal Agent Containing Momordicae Semen Extract

The Momordicae semen extract of the present invention was prepared into a transdermal agent.

[Composition 1]

Momordicae semen extract (0.4 g), sodium polyacrylate (1.3 g), glycerin (3.6 g), aluminum hydroxide (0.04 g), methyl paraben (0.2 g), water (14 g).

[Composition 2]

Momordicae semen extract (0.8 g), propylene glycol (1.6 g), liquid paraffin (0.8 g), isopropyl myristate (0.4 g), gelba 1430 (16.4 g).

PREPARATION EXAMPLE 6

Preparation of Transdermal Agent Containing Momordica Saponin I

The *momordica* saponin I of the present invention was prepared into a transdermal agent.

[Composition 1]

*Momordica* saponin I (20 mg), sodium polyacrylate (1.3 g), glycerin (3.6 g), aluminum hydroxide (0.04 g), methyl paraben (0.2 g), water (14 g).

[Composition 2]

*Momordica* saponin I (40 mg), propylene glycol (1.6 g), liquid paraffin (0.8 g), isopropyl myristate (0.4 g), gel bar 1430 (16.4 g).

Industrial Applicability

As apparent from the above description, the Momordicae semen extract in accordance with the present invention and *momordica* saponin I isolated therefrom are very useful for the prevention and treatment of gastritis or gastric ulcer as they have superior effects in preventing the damage of gastric mucosa induced by alcohols and non-steroidal anti-inflammatory drugs (NSAID) and also inhibiting the secretion of gastric acid.

Those skilled in the art will appreciate that the concepts and specific embodiments disclosed in the foregoing description may be readily utilized as a basis for modifying or designing other embodiments for accomplishing the same purposes of the present invention. Those skilled in the art will also appreciate that such equivalent embodiments do not depart from the spirit and scope of the present invention according to the appended claims.

What is claimed is:

1. A method of treating gastritis or gastric ulcer in a patient in need thereof consisting essentially of administering a therapeutically effective amount of Momordicae semen extract as an active ingredient.

2. The method of claim 1, wherein the Momordicae semen extract is obtained by extracting Momordicae semen with water or alcohol solution.

3. The method of claim 2, wherein said alcohol is a $C_1$-$C_6$ alcohol.

4. The method of claim 1, wherein the Momordicae semen extract comprises *momordica* saponin I represented by the following formula (1):

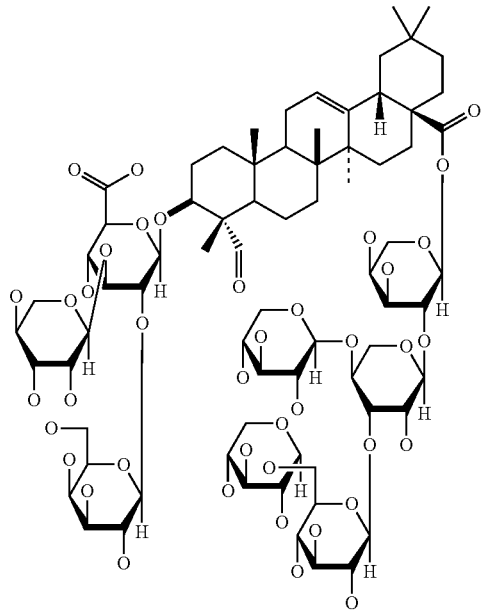

(1)

as an active ingredient.

5. The method of claim 4, wherein the *momordica* saponin I is administered in a amount of 0.05-1 mg of *momordica* saponin I per 1 kg of body weight of the patient.

* * * * *